United States Patent [19]
Chalk et al.

[11] Patent Number: 6,118,027
[45] Date of Patent: Sep. 12, 2000

[54] PREPARATION OF UNSATURATED ALDEHYDES FROM PROPARGYL ALCOHOL AND CONJUGATED DIOLEFINS

[75] Inventors: Alan John Chalk, Lewes, Del.; Joseph Anthony Virgilio, Wayne, N.J.

[73] Assignee: Givaudan Roure (International) SA, Vernier-Geneve, Switzerland

[21] Appl. No.: 09/294,966

[22] Filed: Apr. 20, 1999

Related U.S. Application Data

[60] Provisional application No. 60/082,324, Apr. 20, 1998.

[51] Int. Cl.⁷ ..................................................... C07C 45/67
[52] U.S. Cl. ........................................... 568/443; 568/450
[58] Field of Search ..................... 568/384, 310, 568/427, 450, 443, 467

[56] References Cited

U.S. PATENT DOCUMENTS

| | | | |
|---|---|---|---|
| 2,406,106 | 8/1946 | Rummelsburg | 260/617 |
| 4,007,137 | 2/1977 | Sanders et al. | 252/522 |
| 4,749,814 | 6/1988 | Chabardes | 568/384 |
| 5,077,438 | 12/1991 | Steck et al. | 568/450 |

FOREIGN PATENT DOCUMENTS

| | | |
|---|---|---|
| 0 240 431 | 10/1987 | European Pat. Off. . |
| 0 444 460 | 9/1991 | European Pat. Off. . |
| 526 168 | 6/1931 | Germany . |
| 1204754 | 9/1970 | United Kingdom . |

OTHER PUBLICATIONS

Derwent Abstract of Japanese Patent No. 10158684, (Jun. 16, 1998).

*Primary Examiner*—Sreeni Padmanabhan
*Attorney, Agent, or Firm*—Mark E. Waddell; Stephen M. Haracz; Bryan Cave LLP

[57] ABSTRACT

Unsaturated aldehydes are prepared by mixing propargyl alcohol, a catalyst and a conjugated diolefin and heating the mixture for a time and at a temperature sufficient to form an unsaturated aldehyde. The diolefin may be 2-methylpentadiene, 2(5,5 dimethyl 5 hydroxy pentyl)1,3 butadiene or myrcene. The catalyst may be inorganic, organic, organometallic or mixtures thereof.

12 Claims, No Drawings

PREPARATION OF UNSATURATED ALDEHYDES FROM PROPARGYL ALCOHOL AND CONJUGATED DIOLEFINS

This application claims the benefit of U.S. Provisional Application No. 60/082,324 filed Apr. 20, 1998.

BACKGROUND OF THE INVENTION

The present invention relates to the synthesis of unsaturated aldehydes from acetylenic alcohols and conjugated diolefins. More particularly, it relates to the synthesis of unsaturated aldehydes from the reaction of propargyl alcohol with conjugated diolefins.

Numerous 2+4 cycloadditions have been known since long before the advent of the pericyclic theory; they are among the most powerful of synthetic reactions. The most important of these is the Diels-Alder reaction. Although the Diels-Alder reaction occurs in the unsubstituted case, it is most successful when the diene and the alkene (referred to in this context as the dienophile) bear substituents of complementary electronic influence. Although these are most commonly an electron-donating group on the diene and an electron-withdrawing group on the dienophile, there are also a number of instances that illustrate inverse electron demand, that is electron-withdrawing groups on the diene and donating groups on the dienophile.

Unsaturated aldehydes can be prepared by the Diels-Alder reaction. An example of such a preparation is the reaction of acrolein with conjugated dienes. Acrolein is an α,β-unsaturated carbonyl compound which is a highly toxic lachrymatory liquid and which has a low boiling point (53° C.). Examples of the preparation of unsaturated aldehydes by reaction of acrolein with conjugated dienes are the preparation of Cyclal C (reaction 1 below); the preparation of myraldene (reaction 2 below); and the preparation of cyclohexal (reaction 3 below).

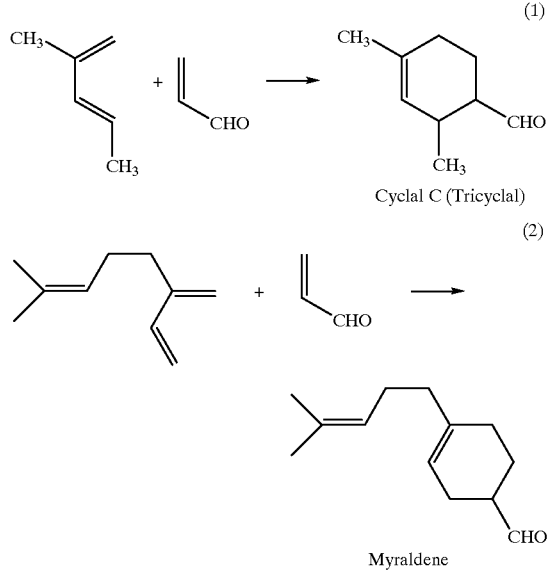

Cyclal C (Tricyclal)

Myraldene

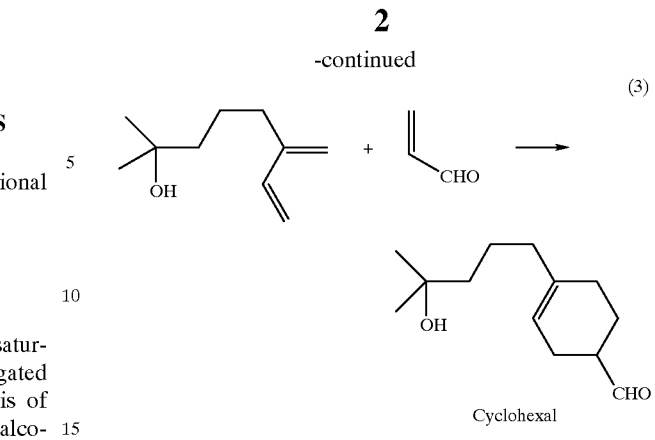

Cyclohexal

Unfortunately, the highly toxic nature and low boiling point of acrolein make it a very dangerous compound. The fumes of acrolein are copiously produced at normal temperatures, i.e., above 0° C. For this reason, restrictions have been placed on transporting acrolein, and acrolein is no longer generally available. However, the need to prepare unsaturated aldehydes still remains and is very important in many industries, such as in the fragrance industry.

Propargyl alcohol is a compound which is less toxic and has a higher boiling point (114–115° C.) than acrolein. Propargyl alcohol can be converted to acrolein under particular reaction parameters. Catalysts used for such transformations include vanadium compounds, such as those which are discussed in Chabardes, et al., British Patent Specification 1,204,754, and a combination of titanium and copper catalysts, such as those described in Chabardes, et al., U.S. Pat. No. 4,749,814, the disclosures of each of which are incorporated herein by reference. There are, however, disadvantages to the reactions disclosed in these documents, which include, for example, that under the disclosed reaction parameters, acrolein polymerizes readily even in the presence of an inhibitor such as hydroquinone thereby limiting the useful yield of acrolein.

SUMMARY OF THE INVENTION

We have now found that unsaturated aldehydes can be synthesized from propargyl alcohol in the presence of a conjugated diolefin. The reaction process of the present invention employs a reactant which is readily available, less toxic and which has a higher boiling point than acrolein to allow for safe transportation. In addition the synthetic method of the present invention avoids the direct use of acrolein in preparing unsaturated aldehydes, while maintaining the ability to prepare unsaturated aldehydes in significant yields.

In this reaction which occurs in a one-pot system, propargyl alcohol is converted to acrolein in the presence of a conjugated diene, and upon conversion to acrolein, the acrolein immediately reacts, as soon as it is formed, with the diene to produce an unsaturated aldehyde. Proceeding in accordance with the present invention, allows one to avoid low yields which occur in the reactions disclosed in the documents noted above, by avoiding polymerization of acrolein. It is also possible to obtain higher yields of the desired unsaturated aldehydes than would be otherwise obtainable by a normal two step synthesis. A further advantage of this process, is that it avoids the potential toxic dangers of acrolein because the acrolein formed is an intermediate which only has a transient existence within the vessel in which the reaction takes place, and is present at a very low concentration before it further reacts to form the unsaturated aldehydes.

DETAILED DESCRIPTION OF THE INVENTION

The unsaturated aldehydes of the structures (I) and (II) which can be formed by the present synthetic method as illustrated in equations 4 and 5 below, are perfumery ingredients or intermediates for perfumery ingredients. In accordance with the present invention, propargyl alcohol is combined with a conjugated diolefin and the components are mixed and heated in the presence of a catalyst which isomerizes the propargyl alcohol to acrolein (as illustrated in reaction 4) which reacts with the conjugated diolefin in a Diels-Alder reaction to give the desired unsaturated aldehyde products (as illustrated in reaction 5).

$$CH_2=CH-CH_2OH \xrightarrow{O} CH_2=CH-CHO \quad (4)$$

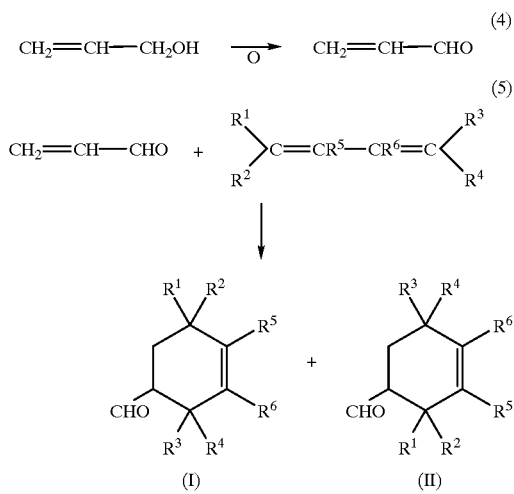

In the unsaturated aldehyde products of reaction (5), $R^1$, $R^2$, $R^3$, $R^4$, $R^5$, and $R^6$ may be the same or different, and may be hydrogen, an alkyl radical ($CnH_2n+1$), a substituted alkyl radical ($CnH_2n$ X where X can be, for example, OH or OR), an aryl radical ($C_6H_5$) or a substituted aryl radical (such as $C_6H_4$ X or $C_6H_3$ XY where X and Y are substituents such as OH and OR) which, in turn, depends on the diolefin employed.

Where $R^1$–$R^6$ are alkyl radicals, $R^1$–$R^5$ preferably are methyl, ethyl or propyl, and $R^6$ preferably is methyl, ethyl or 4-methyl-3-pentyl. Where $R^6$ is a substituted alkyl radical, it preferably is 4-methyl-4-hydroxypentyl or 4-methyl-4-methoxypentyl. Where $R^6$ is a substituted aryl radical, it preferably is phenyl, 2-hydroxyphenyl, 2-methoxyphenyl, 4-hydroxyphenyl or 4-methoxyphenyl.

Other acetylenic alcohols which may be employed are indicated by the general formula shown below wherein when $R^1$ and $R^2$ are hydrogen, $R^3$ is preferably methyl. When $R^2$ and $R^3$ are hydrogen, $R^1$ is preferably methyl.

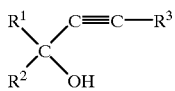

Diolefins which may be employed in the process of the present invention include 2-methylpentadiene, myrcene and 2(5,5 dimethyl 5 hydroxy pentyl)1,3 butadiene.

Solvents which may be used in the process include hydrocarbon solvents, preferably having boiling points of above about 200° C. A solvent preferably employed is dixylylethane.

Catalysts which may be employed in carrying out these processes include inorganic and/or derivatives thereof; organic and/or derivatives thereof; and organometallic catalysts. The catalysts may be employed alone or in combinations.

The process may be carried out at a temperature sufficient to initiate the reaction. The temperature may be of from about 100° C. to about 150° C. More preferably, the temperature of the reaction is from about 120° C. to about 140° C., and most preferably it is from about 125° C. to about 135° C.

The time required for the reaction to take place is not critical and a sufficient time may be from a few seconds (that is, the reaction occurs immediately), to as long as a day. Generally, the reaction occurs over a period of from 30 minutes to 4 hours, and more particularly from 2 hours to 4 hours. The time for the reaction, of course, depends on the temperature at which the process is carried out and on the particular catalyst employed in the process.

The amount of propargyl alcohol and of conjugated diolefin which may be employed, will depend on the amount of unsaturated aldehyde desired to be produced, based on the yield of unsaturated aldehyde that the reaction provides.

EXAMPLES

The present invention is described further in the following examples which are presented solely for the purpose of providing a further non-limiting illustration of the invention. In the following examples, yields of the products are based on the amount of propargyl alcohol employed in the processes.

Example 1

This example illustrates the formation of an unsaturated aldehyde under conditions of autogeneous pressure.

3.1 g of titanium isopropoxide, 1.5 g of cuprous chloride, 18.0 g of p-toluic acid, 19.4 g of dixylylethane, 56.0 g of propargyl alcohol, and 82.0 g of 2-methylpentadiene were added to a 500 ml autoclave under nitrogen atmosphere and heated at autogenous pressure to a temperature of 130° C. for 20 hours. The resulting product mixture was then analyzed by gas chromatography using calculations based on dixylylethane as the internal standard. The analysis revealed a 92% conversion for the propargyl alcohol, a 70% conversion for the methylpentadiene, and a yield of Cyclal C of 45.4% which was acceptable.

Example 2

This example illustrates the formation of an unsaturated aldehyde under atmospheric pressure.

0.80 g of titanium isopropoxide, 0.40 g of cuprous chloride, 3.5 g of p-toluic acid, and 10.1 g of dixylylethane were added to a 100 ml 3-neck round bottom flask arranged and fitted with a delivery funnel, a thermometer, and a reflux condenser and having a magnetic stirrer contained within the flask. Propargyl alcohol (11.1 g), myrcene (39.1 g) and dixylylethane (10.0 g) were added to a separatory funnel and the funnel was then shaken to form a mixture. Pressure was intermittently released from the funnel until most or all of the pressure from the reaction in the funnel had been released. The funnel was then left to stand until an upper layer phase and a lower layer phase were formed and separated out from the mixture. The lower layer was then released from the funnel and transferred to the delivery funnel fitted to the flask. The upper layer was transferred directly into the flask.

The reaction components in the flask were then heated and mixed under nitrogen atmosphere to a temperature of 130° C. and the lower layer was then added dropwise from the delivery funnel into the mixture until reflux was noted at the condenser. Further addition was made gradually so that a constant temperature of 130° C. was maintained. The total time for addition of the lower layer from the delivery funnel was about three hours. After a further twenty minutes, a sample of the reaction product was taken from the flask, showing an acceptable yield of 45.5% myraldene by internal standard. The conversion of propargyl alcohol and myrcene were 93% and 71%, respectively.

Comparative Example

This comparative example illustrates a reaction which is carried out in two steps. In this example, no reaction occurs at the reflux temperature of the propargyl alcohol (114–115° C.) but the reaction may be effected by adding the propargyl alcohol gradually to the catalyst in a high boiling solvent at 130° C. To optimize the yield of acrolein, it was distilled off as formed. In spite of this the yield of acrolein was only 22%.

2.5 g of titanium isopropoxide, 1.2 g of cuprous chloride, 80.0 ml of dixylylethane, and 18.8 g of 4-methoxycinnamic acid were combined and mixed with a magnetic stirrer while heating the mixture to 130 E in 3 neck round bottomed flask. The flask was also fitted with a distillation column and a receiver, thermometers and a nitrogen bypass. Propargyl alcohol was added slowly to the mixture in the flask at a rate such that the distillate showed an acrolein content of at least 80–90%. After the addition of approximately 40 ml propargyl alcohol, there was no further conversion indicating that the catalyst had been deactivated. The reaction resulted in an overall conversion of propargyl of 74% and a yield of 22% acrolein based on conversion. In the second step, the reaction of acrolein with the conjugated diolefin normally occurs in a yield of around 50%.

As can be seen, the single step reaction of the present invention avoids the problems attendant the two step reaction, but yet achieves comparable yields of products.

While the invention has been illustrated and described with respect to illustrative embodiments and modes of practice, it will be apparent to those skilled in the art that various modifications and improvements may be made without departing from the scope and spirit of the invention. Accordingly, the invention is not to be limited by the illustrative embodiments and modes of practice.

We claim:

1. A process for preparing an unsaturated aldehyde comprising mixing propargyl alcohol, a catalyst system comprising (1) a titanium derivative, (2) a copper derivative and optionally (3) an inorganic or organic acid and a conjugated diolefin and heating the mixture to form an unsaturated aldehyde.

2. A process according to claim 1 wherein the diolefin is selected from the group consisting of 2-methylpentadiene, myrcene and 2-methyl-6-methylene-7-octen-2-ol.

3. A process according to claim 1 where in the catalyst is selected from the group consisting of inorganic, organic, organometallic and mixtures thereof.

4. A process according to claim 2 where in the catalyst is selected from the group consisting of inorganic, organic, organometallic and mixtures thereof.

5. A process according to claim 4 wherein the catalyst is an inorganic catalyst.

6. A process according to claim 3 wherein the process is carried out at a temperature of from about 100° C. to about 150° C.

7. A process for preparing an unsaturated aldehyde of the formula:

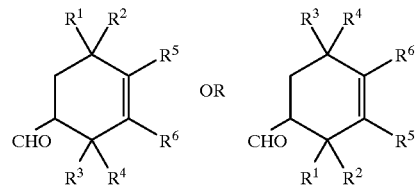

wherein $R^1$, $R^2$, $R^3$, $R^4$, $R^5$, and $R^6$ are selected from the group consisting of hydrogen, alkyl radicals, substituted alkyl radicals, aryl radicals and substituted aryl radicals, comprising mixing propargyl alcohol, a catalyst system comprising (1) a titanium derivative, (2) a copper derivative and optionally (3) an inorganic or organic acid and a conjugated diolefin and heating the mixture to form the unsaturated aldehyde.

8. A process according to claim 7 wherein the diolefin is selected from the group consisting of 2-methylpentadiene and myrcene.

9. A process according to claim 7 wherein the catalyst is selected from the group consisting of inorganic, organic, organometallic and mixtures thereof.

10. A process according to claim 8 wherein the catalyst is selected from the group consisting of inorganic, organic, organometallic and mixtures thereof.

11. A process according to claim 10 wherein the catalyst is an inorganic catalyst.

12. A process according to claim 5 wherein the process is carried out at a temperature of from about 100° C. to about 150° C.

* * * * *